United States Patent [19]

Salmon

[11] Patent Number: 4,606,334

[45] Date of Patent: Aug. 19, 1986

[54] ORTHOPEDIC FOOT SPLINT AND METHOD FOR USING SAME

[75] Inventor: Michael E. Salmon, Flint, Mich.

[73] Assignee: GMI Engineering & Management Institute, Flint, Mich.

[21] Appl. No.: 649,550

[22] Filed: Sep. 11, 1984

[51] Int. Cl.⁴ .................................................. A61F 3/00
[52] U.S. Cl. .................................. 128/80 A; 128/87 C
[58] Field of Search ............... 128/80 R, 80 A, 80 F, 128/80 G, 80 J, 87 R, 88, 87 C; 172/484, 624.5; 414/917, 705

[56] References Cited

U.S. PATENT DOCUMENTS

| | | | |
|---|---|---|---|
| 2,815,021 | 12/1957 | Freeman | 128/80 A |
| 2,963,020 | 12/1960 | Moran | 128/80 J |
| 3,209,749 | 10/1965 | Walker | 128/80 |
| 3,265,063 | 8/1966 | Friedman | 128/80 |
| 3,487,829 | 1/1970 | Barnett | 128/80 R |
| 3,777,747 | 12/1973 | Friedman | 128/80 A |
| 3,812,850 | 5/1974 | Reiman | 128/80 A |
| 3,910,267 | 11/1975 | Reiman | 128/80 A |
| 3,973,559 | 8/1976 | Reiman | 128/80 A |
| 4,040,416 | 8/1977 | Zentman | 128/80 R |
| 4,249,523 | 2/1981 | Bidwell | 128/80 A |
| 4,303,065 | 12/1981 | Ericson | 128/80 A |
| 4,336,795 | 6/1982 | Nichols | 128/80 A |
| 4,412,536 | 11/1983 | Kurtz et al. | 128/80 A |
| 4,520,803 | 6/1985 | Quest | 128/80 A |

FOREIGN PATENT DOCUMENTS

2749411 . 5/1979 Fed. Rep. of Germany ... 128/80 A

Primary Examiner—Clifford D. Crowder
Attorney, Agent, or Firm—Burton, Parker & Schramm

[57] ABSTRACT

An apparatus having a pair of brackets for attachment to the feet of the patient which are interconnected by a number of links pivotably attached to the shoe brackets. The shoe brackets are maintained in constant parallel spaced apart relation preventing transverse movement and relative rotation of the patient's feet about the vertical and longitudinal axis. The patient's feet may freely move relative to one another along the longitudinal and vertical axis as well as rotate about the transverse axis.

10 Claims, 6 Drawing Figures

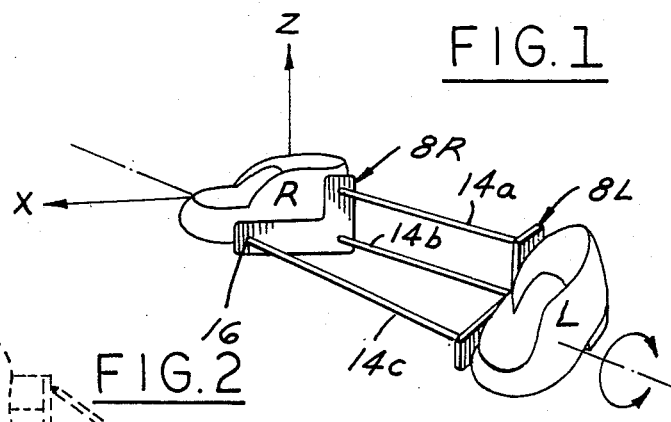
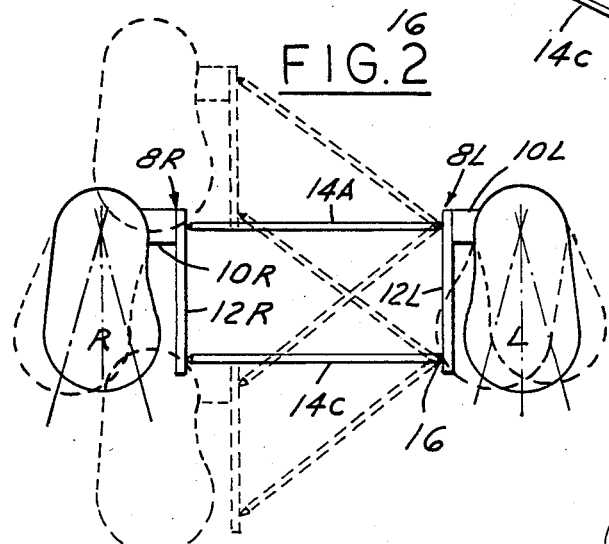
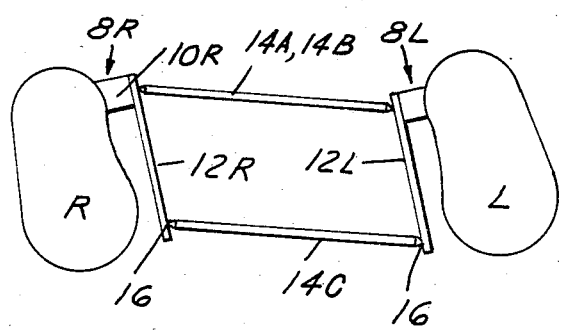
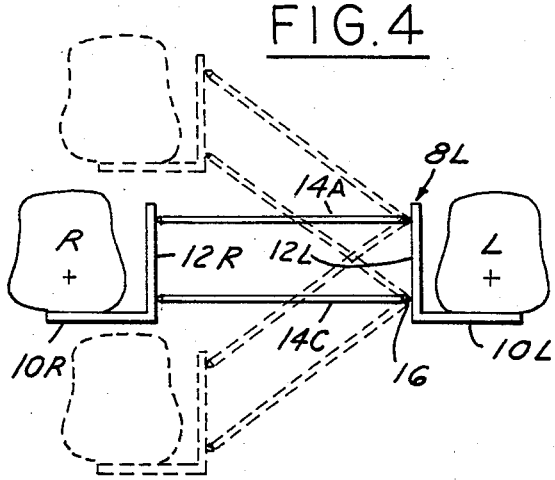
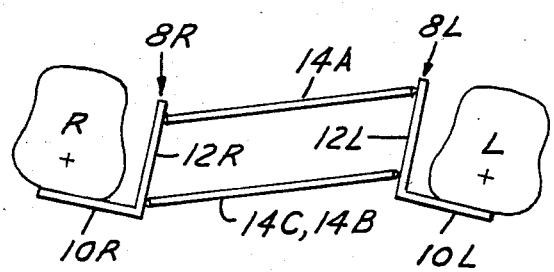
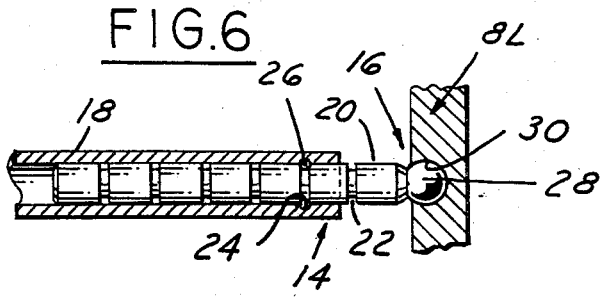

ORTHOPEDIC FOOT SPLINT AND METHOD FOR USING SAME

DESCRIPTION

1. Field of Invention

This invention relates to orthopedic splints used to maintain the patient's feet in a predetermined relationship and more particularly to such an apparatus allowing the feet to move in a limited range relative to one another.

2. Background of Invention

Orthopedic foot splints are useful in correcting bone deformities and improper walking habits particularly in infants by holding the patient's feet in proper spaced apart orientation. A number of devices such as those shown in U.S. Pat. No. 3,209,749; U.S. Pat. No. 3,265,063; U.S. Pat. No. 3,777,747; U.S. Pat. No. 3,973,559 and U.S. Pat. No. 4,336,795 have been developed for retaining the patient's feet in proper spaced apart relation. The problem inherent with the above-listed devices is that the patient's feet cannot move relative to one another and the development of the patient's leg muscles and walking skills is hindered. In order to allow some relative movement of the patient's feet the device shown in U.S. Pat. No. 4,040,416 employed a flexible-leaf spring interconnecting the patient's feet to allow limited vertical movement of the feet. However, the feet could not be rotated nor could a forward stepping motion be made while wearing the device. To allow the patient to have more freedom of movement, the devices shown in U.S. Pat. Nos. 4,249,523 and 4,412,536 were developed which control the toe-in/toe-out relationship of the feet but otherwise allow virtually full freedom of movement. These last mentioned devices however, do not maintain the relative spacing between the patient's feet nor do these devices prevent a patient from rotating his or her feet along the longitudinal axis relative to one another as occurs when the patient walks on the outside edges of the feet.

SUMMARY OF THE INVENTION

I have invented a novel apparatus and method for controlling the relative relationship and movement of a patient's feet which is useful in correcting bone deformities and irregular walking habits. My treatment method is to hold the patient's feet in spaced apart relation using an orthopedic device which prevents the patient from moving his or her feet relative to one another along the transverse axis and similarly prevents the rotation of the feet relative to one another about the vertical and longitudinal axis. The patient is allowed to move his or her feet through a limited free range of rotation about the transverse axes as well as moving the feet relative to one another along the longitudinal and the vertical axis.

The apparatus which I have invented attaches to both feet of the patient using some form of attachment means. The attachment means are interconnected in such a manner as to allow the patient's feet to move relative to one another consistent with the above-described method. The attachment means may be interconnected with three or more links, each pivotably attached at one end to the attachment means connected to the right foot and pivotably attached at the other end to the attachment means connected to the patient's left foot.

BRIEF DESCRIPTION OF THE DRAWINGS

FIG. 1 is a perspective view of a pair of shoes attached to an embodiment of the orthopedic foot splint.

FIG. 2 is a top plan view of the orthopedic foot splint showing the rnage of motion of the patient's feet in phantom outline.

FIG. 3 is a top plan view of the orthopedic foot splint showing the patient's feet rotated counter-clockwise about the vertical axis.

FIG. 4 is a front view of the orthopedic foot splint showing the range of vertical motion in phantom outline.

FIG. 5 is a front view of the orthopedic foot splint showing the patient's shoes rotated clockwise about the longitudinal axis.

FIG. 6 is an enlarged cutaway section of a portion of the linkage pivotably attached to the shoe bracket.

DETAILED DESCRIPTION OF THE PREFERRED EMBODIMENT

With reference to the drawings, the preferred embodiment of the present invention will be described. FIG. 1 shows the right shoe R and a left shoe L attached to the orthopedic foot splint. The splint is comprised of a right shoe bracket 8R and a left shoe bracket 8L which are securely attached to the right and left shoe respectively. A perferred design of shoe bracket depicted in the drawings is generally L-shaped when viewed along the longitudinal (X) axis. Each shoe bracket 8R and 8L, is provided with a lower surface 10R and 10L for attachment to the sole of the patient's shoe. Extending generally perpendicular to the shoe bracket lower surface 10R and 10L is a shoe bracket inner surfaces 12R and 12L which faces inwardly, i.e., toward the inner surface of the shoe bracket attached to the opposite foot.

The shoe brackets 8R and 8L are connected to one another by links 14 identified as (a), (b), and (c). Each link has two ends. One end is universally, pivotably attached to the inner surface 12R of the right bracket 8R and the other end is similarly attached to the left bracket. The links are attached to the inner surface of the shoe brackets using a pivot 16 such as a ball and socket or the like so that the link is universally pivotably, (i.e. having two degrees of freedom, link 14(a), can rotate about the transverse axis (Y) as well as rotate about the vertical axis (Z), as opposed to a hinge-type pivot with one degree of freedom). Inner surfaces 12R and 12L are defined by the plane in which pivots 16 lie. Inner surface 12R and 12L need not be a smooth continuous planar surface as shown in the drawing but could alternatively be three or more remotely located co-planar points which define a plane. The links 14(a), (b), and (c) are preferably equal length, parallel, spaced apart from one another, and do not lie in a common plane. It is important that all the links not lie in a common plane in order to prevent the inner surface 12R and 12L of the shoe brackets from rotating into a non-parallel relationship. More than three links can be used, however, 3 is the minimum number and is preferred.

Still referring to FIG. 1, the Z axis is referred to as the vertical axis of the patient's foot. The longitudinal axis is identified with the letter X and the transverse axis is identified with the letter Y. The spacing of the patient's feet along the transverse axis Y is controlled by the length of links 14. As indicated by the arrow drawn about the transverse axis (Y), the patient's feet are capable of freely rotating relative to one another for a limited angle about the transverse axis. During the rotation about the transverse axis, spacing of the feet is maintained constant, only an insignificant change in the spacing occurs as a result of the torsional pendulum effect of the three spaced apart links.

Referring to the FIG. 2, a plan view of the apparatus is shown with both feet in the straight ahead position. Note that the patient's shoes may be alternatively attached to the shoe bracket in the toe-in or toe-out position if the patient's medical condition so warrants. Referring to the phantom outline as shown, the patient may move his right foot forward or backward within a limited range as shown by the phantom outline of the shoe bracket and links. The patient is free to move his or her feet relative to one another along the longitudinal axis within the angular range of the pivot 16 provided at the attachment point of links 14 and shoe brackets 8R and 8L.

As shown in FIG. 3, the patient may rotate his or her feet in unison about the vertical axis relative to the patient's torso. The orthopedic foot splint, however, prevents the patient from moving his or her feet in the toe-in or toe-out position. The inner surface of the shoe brackets are constantly parallel throughout the patient's limited range of motion. Within the angular range of travel of pivots 16, the patient's feet may be freely rotated in unison. Rotation of one foot relative to the other, however, is prohibited.

The user wearing the orthopedic foot splint may lift one foot vertically relative to the other as shown in FIG. 4. The range of relative motion of the patient's feet along the vertical axis is depicted by the phantom outlines. Note that rotation of the patient's feet relative to one another is constrained by the device. As shown in FIG. 5, both of the patient's feet may be rotated about the longitudinal axis as shown. The patient, however, is prevented from walking on the outside of both feet simultaneously or the inside of both feet simultaneously. If a patient has a tendency of walking on the outside edge of one or both of his or her feet, this device will prevent and eventually attempt to cure such a tendency.

In order to make the device easily adaptable to a variety of size patients as well as being adjustable to allow for the rapid growth of an infant patient, linkages 14 are preferably made so they can be adjusted in length. While it is possible to vary the length of the linkage using a bolt which fits into an internally threaded tube, a simple and convenient telescoping link is shown in FIG. 6. Link 14 is formed of a tube 18 into which rod 20 telescopically cooperates. The peripheral surface of rod 20 is provided with a number of axial spaced annular grooves 22. Tube 18 is provided with internal annular groove 24 for retention of a split snap ring 26. Rod 20 may be telescopically moved within the bore of tube 18 to vary the links' length in discreet increments. Preferably links 14 are equal in length and parallel so that shoe brackets 10 and 12 are always maintained parallel to one another.

FIG. 6 also shows the detail of a suitable pivot 16 connecting link 14 to shoe bracket 12. A ball 28 is formed in the end of rod 20 which pivotally engages a corresponding socket 30 formed in shoe bracket 12. The ball could alternatively be formed as part of shoe bracket 12 and the socket formed in the end of rod 20, or a host of other pivot designs could be employed. It is important to use a pivot design which will enable a rotation of the link relative to the shoe bracket in two degrees of freedom for sufficient range to allow the patient to make the above-described stepping and lifting motions. The mechanism for attaching the shoe bracket to the patient's shoe has not been described as various mechanisms are well-known in the art as depicted in U.S. Pat. Nos. 4,040,416 and 4,249,523. Similarly, adjustments to vary the rotational position of one shoe relative to the other about the vertical axis such as shoe wedges, mechanical adjustments and the like are not described as such are mere matters of design choice.

Not only is the above-described apparatus novel, my method for treating bone deformities and abnormal walking habits is similarly novel. My treatment method comprises the step of holding the patient's feet with an orthopedic splint to prevent the relative rotation of the feet about the vertical and longitudinal axis while also preventing relative motion along the transverse axis. While restraining motions described above, my method of treatment allows limited free rotation of the patient's feet about the transverse axis and allows relative movement along the longitudinal and vertical axes. Employment of my treatment method provides sufficient restraint to correct the bone deformity and/or walking abnormality while allowing sufficient range of motion so that the patient may develop motor skills and muscles used in walking and crawling.

It will also be understood, of course, that while the form of the invention herein shown and described constitutes a preferred embodiment of the invention, it is not intended to illustrate all possible forms thereof. It will also be understood that the words used are words of description rather than limitation and various changes may be made without departing from the spirit and scope of the invention disclosed.

I claim:

1. An orthopedic foot splint for treating a patient's feet, comprising:
   a right and left attachment means for fixed connection to the feet of the patient; and
   linkage means for interconnecting said attachment means to maintain same in constant spaced apart and parallel relation with respect to a longitudinal axis while preventing relative rotation about said longitudinal axis and allowing free limited rotation about a transverse axis and allowing relative longitudinal and vertical movement therebetween.

2. An orthopedic foot splint for treating a patient's feet, comprising:
   a right and left attachment means for fixed connection to the feet of the patient; and
   linkage means for interconnecting said attachment means to maintain same in constant spaced apart and parallel relation with respect to a longitudinal axis while allowing free limited rotation about a transverse axis and allowing relative longitudinal and vertical movement therebetween, said linkage means having three or more links, each having two ends, one end universally, pivotably attached to the right attachment means and the other end universally, pivotably attached to the left attachment means, said links being spaced apart and not all lying in a common plane.

3. The invention of claim 2 wherein said links are generally parallel to one another and equal in length.

4. The invention of claim 3 wherein said attachment means further comprises a bracket which can be removably, securely attached to a patient's shoe.

5. The invention of claim 4 wherein said shoe bracket is generally L-shaped having a lower surface for attachment to the sole of the patient's shoe and an inner surface generally perpendicular thereto facing the inner surface of the shoe bracket on the opposite foot for pivotable attachment of said links.

6. The invention of claim 5 having three links universally, pivotably attached to and interconnecting the inner surfaces of said shoe brackets.

7. The invention of claim 6 wherein the universal, pivotably attachment of said link to the inner surface of the shoe bracket is provided by a ball and socket joint, thereby allowing limited free movement of the patient's feet while maintaining the inner surfaces of the shoe brackets spaced apart and parallel.

8. The invention of claim 7 wherein said links are further provided with means for length adjustment to vary the relative spacing between the patient's feet.

9. An orthopedic foot splint for treating a patient's feet, comprising:
a right and left attachment means for connection to the feet of the patient and linkage means for interconnecting said attachment means to prevent relative transverse movement and relative rotation of the patient's feet about the vertical and longitudinal axes, while allowing limited free relative rotation about the transverse axis and limited relative longitudinal and vertical movement.

10. A method for treating bone deformities and the like, comprising the step of holding the patient's feet in spaced apart relation using an orthopedic splint which restrains relative rotation of the feet about the vertical and longitudinal axes and prevents relative transverse motion, while allowing limited free relative rotation about the transverse axis and limited relative longitudinal and vertical movement.

* * * * *

UNITED STATES PATENT AND TRADEMARK OFFICE
CERTIFICATE OF CORRECTION

PATENT NO. : 4,606,334

DATED : August 19, 1986

INVENTOR(S) : MICHAEL E. SALMON

It is certified that error appears in the above-identified patent and that said Letters Patent is hereby corrected as shown below:

In column 5, line 11, change "pivotably" to ---pivotable---.

Signed and Sealed this

Twenty-eighth Day of October, 1986

[SEAL]

Attest:

DONALD J. QUIGG

Attesting Officer     Commissioner of Patents and Trademarks